United States Patent [19]
Esenaliev

[11] Patent Number: 6,165,440
[45] Date of Patent: *Dec. 26, 2000

[54] RADIATION AND NANOPARTICLES FOR ENHANCEMENT OF DRUG DELIVERY IN SOLID TUMORS

[75] Inventor: Rinat O. Esenaliev, Galveston, Tex.

[73] Assignee: Board of Regents, The University of Texas System, Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 09/112,491

[22] Filed: Jul. 9, 1998

Related U.S. Application Data

[60] Provisional application No. 60/052,202, Jul. 9, 1997.

[51] Int. Cl.[7] ................ A61K 51/00; C07H 21/04; H05B 6/00; A61N 5/00
[52] U.S. Cl. ............... 424/1.11; 264/473; 264/488; 600/1; 536/23.1; 536/24.5; 514/44
[58] Field of Search .............. 435/6, 91.1; 514/44; 604/21, 15, 102; 536/24.5

[56] References Cited

U.S. PATENT DOCUMENTS

| | | | |
|---|---|---|---|
| 4,971,991 | 11/1990 | Umemura et al. | 514/410 |
| 5,380,411 | 1/1995 | Schlief | 204/157.15 |
| 5,403,590 | 4/1995 | Forse | 424/422 |
| 5,474,765 | 12/1995 | Thorpe | 424/78.17 |
| 5,487,390 | 1/1996 | Cohen et al. | 600/458 |
| 5,543,158 | 8/1996 | Gref et al. | 424/501 |
| 5,565,215 | 10/1996 | Gref et al. | 424/501 |
| 5,578,325 | 11/1996 | Domb et al. | 424/501 |
| 5,599,712 | 2/1997 | Greenberger | 435/267 |
| 5,614,502 | 3/1997 | Flotte et al. | 514/34 |
| 5,651,986 | 7/1997 | Brem et al. | 424/484 |
| 5,836,905 | 11/1998 | Lemelson et al. | 604/21 |

OTHER PUBLICATIONS

Hopper et al., "Mechanism of Inclusion Damage in Laser Glass," *Journal of Applied Physics*, 41(10):4023–4037 (1970).
Takahashi et al., "Emulsion and Activated Carbon in Cancer Chemotherapy," *CRC Critical Reviews in Therapeutic Drug Carrier Systems*, 2(3):245–274 (1986).
Esenaliev et al., "Laser Ablation of Atherosclerotic Blood Vessel Tissue Under Various Irradiation Conditions," *IEEE Transactions on Biomedical Engineering*, 36(12):1188–1194 (1989).
Dvorak et al., "Structure of Solid Tumors and Their Vasculature: Implications for Therapy with Monoclonal Antibodies," *Cancer Cells*, 3(3):77–85 (1991).
Esenaliev et al., "Studies of Acoustical and Shock Waves in the Pulsed Laser Ablation of Biotissue," *Lasers in Surgery and Medicine*, 13:470–484 (1993).
Esenaliev et al., "Effect on Erthrocytes of Acoustic Waves Generated upon Absorption of Laser Radiation," *Lasers in the Life Sciences*, 63):153–161 (1994).
Esenaliev et al., "Laser Ablation of Aqueous Solutions with Spatially Homogeneous and Hetergeneous Absorption," *Applied Physics B*, 59:73–81 (1994).
Gref et al., "Biodegradable Long–Circulating Polymeric Nanospheres," *Science*, 263:1600–1603 (1994).
Jain, "Barriers to Drug Delivery in Solid Tumors," *Scientific American*, 271:58–65 (Jul. 1994).
Mitragotri et al., "Ultrasound–Mediated Transdermal Protein Delivery," *Science*, 269:850–853 (1995).
Thorpe et al., "Antibody–Directed Targeting of the Vasculature of Solid Tumors," *Breast Cancer Research and Treatment*, 36:237–251 (1995).
Curti, "Physical Barriers to drug Delivery in Tumors," pp. 709–719, in Chabner et al., eds., *Cancer Chemotherapy and Biotherapy*, Philadelphia: Raven Publishers (1996).
Folkman, "Fighting Cancer by Attacking Its Blood Supply," *Scientific American*, 275:150–154 (Sep. 1996).
Jain, "Delivery of Molecular Medicine to Solid Tumors," *Science*, 271:1079–1080 (1996).
Pasqualini et al., "Organ Targeting in vivo Using Phage Display Peptide Libraries," *Nature*, 380:364–366 (1996).
Johnson et al., "Synergistic Effects of Chemical Enhancers and Therapeutic Ultrasound on Transdermal Drug Delivery," *Journal of Pharmaceutical Sciences*, 85(7):670–679 (1996).
Oku et al., "Application of Long–Circulating Liposomes to Cancer Photodynamic Therapy," *Biol. Pharm. Bull.*, 20(6):670–673 (1997).
Arap et al., "Cancer Treatment by Targeted Drug Delivery to Tumor Vasculature in a Mouse Model," *Science*, 379:377–380 (1998).

*Primary Examiner*—George C. Elliott
*Assistant Examiner*—Janet Epps
*Attorney, Agent, or Firm*—Braman & Rogalskyj, LLP

[57] ABSTRACT

The present invention discloses a method/system utilizing interaction of electromagnetic pulses or ultrasonic radiation with nano- and microparticles for enhancement of drug delivery in solid tumors. The particles can be attached to antibodies directed against antigens in tumor vasculature and selectively delivered to tumor blood vessel walls. Cavitation induced by ultrasonic waves or local heating of the particles by pulsed electromagnetic radiation results in perforation of tumor blood vessels, microconvection in the interstitium, and perforation of cancer cell membrane, and therefore, provides enhanced delivery of macromolecular therapeutic agents from blood into cancer cells with minimal thermal and mechanical damage to normal tissues.

15 Claims, 18 Drawing Sheets

RADIATION AND NANOPARTICLES FOR ENHANCEMENT OF DRUG DELIVERY IN SOLID TUMORS

CROSS-REFERENCE TO RELATED APPLICATION

This non-provisional patent application claims benefit of provisional patent application U.S. Ser. No. 60/052,202, filed Jul. 9, 1997, now abandoned.

BACKGROUND OF THE INVENTION

1. Field of the Invention

The present invention relates generally to the fields of immunology and cancer therapy. More specifically, the present invention relates to a system utilizing interaction of electromagnetic pulses or ultrasonic radiation with nanoparticles to enhance anti-cancer drug delivery in solid tumors and uses of such a system.

2. Description of the Related Art

Many promising therapeutic agents have been proposed for cancer therapy for the past two decades. Their potential is proven in numerous preclinical studies. However, limited success has been achieved in solid tumor therapy. The presence of physiological barriers to drug delivery in tumors substantially limits efficacy of the anti-cancer drugs. To penetrate into cancer cells in a solid tumor, therapeutic agents have to pass through blood vessel wall, interstitial space, and cancer cell membrane. Penetration of anti-cancer drugs through these physiological barriers is poor especially for the most promising macromolecular therapeutic agents such as monoclonal antibodies, cytokines, antisense oligonucleotides, and gene-targeting vectors.

Methods have been reported for delivery of anti-cancer drugs with low molecular weight in solid tumors. Many of them are based on selective delivery of particles loaded with the drugs in tumors. It has been demonstrated that particles coated with a surfactant have prolonged circulation time and selectively accumulate in tumors because of increased leakage of tumor vasculature in comparison with the normal one. These long-circulating particles avoid rapid clearance by reticuloendothelial system. This approach is referred to as "passive" delivery of particles in tumors.

The "active" delivery is based on attachment of long-circulating particles to antibodies directed against antigens in tumor vasculature. Results of studies on animals bearing tumors derived from human cancer cells demonstrate feasibility of active delivery of anti-cancer drugs to tumor vasculature. These antibodies and short peptide sequences can be used for targeting anti-cancer drugs in patients.

The prior art is deficient in the lack of effective means of enhancing the delivery of anti-cancer drugs (especially macromolecular ones) from tumor blood vessels into cancer cells with minimal damage to normal tissues. The present invention fulfills this long-standing need and desire in the art.

SUMMARY OF THE INVENTION

The present invention is directed to a method or system of utilizing the interaction of electromagnetic pulses or ultrasonic radiation with nanoparticles and microparticles for enhancement of drug delivery in solid tumors. The particles can be attached to antibodies directed against antigens in tumor vasculature and selectively delivered to tumor blood vessel walls. Cavitation induced by ultrasonic waves or local heating of the particles by pulsed electromagnetic radiation results in perforation of tumor blood vessels, microconvection in the interstitium, and perforation of cancer cell membrane. This method provides enhanced delivery of macromolecular therapeutic agents from the blood into cancer cells with minimal thermal and mechanical damage to normal tissues.

In one embodiment of the present invention, there is provided a method of enhancing anti-cancer drug delivery in a solid tumor, comprising the steps of administrating at least one anti-cancer drug to the tumor; injecting nanoparticles or microparticles to the tumor intravenously; and irradiating the tumor with radiation.

Generally, the anti-cancer drug is selected from the group consisting of a monoclonal antibody, a cytokine, an antisense oligonucleotide, a gene-targeting vector and any other macromolecular therapeutic agent. Generally, the tumor occurs in the organ selected from the group consisting of breast, lung, brain, liver, skin, kidney, GI organ, prostate, bladder, gynecological organ and any other hollow organ.

Preferably, the nanoparticles or microparticles are long-circulating particles with or without antibody coating, wherein the antibody is directed against tumor vasculature. The nanoparticles or microparticles can be metal particles, carbon particles, graphite particles, polymer particles loaded with an absorbing dye, liquid particles loaded with an absorbing dye or porous particles having gas-filled pores. The nanoparticle has a diameter from about 0.1 nm to about 7000 nm.

Preferably, the radiation is optical pulsed radiation generated from a laser or non-laser source. Specifically, the optical radiation is in the spectral range from 0.2 $\mu$m to 2 $\mu$m and delivered through the skin surface or via optical fibers inserted in a needle or endoscopes to the tumor.

Preferably, the radiation is ultrasonic radiation generated from an ultrasonic transducer. Specifically, the ultrasonic radiation is in the frequency range from 20 to 500 kHz and delivered through the skin surface to the tumor.

In another embodiment of the present invention, there is provided a system for enhancement of anti-cancer drug delivery in a solid tumor, comprising a source of radiation; an electronic system or means for monitoring of the radiation; a system or means for delivery of the radiation to the tumor; nanoparticles or microparticles absorbing the radiation; an injection system or means for administration of the anti-cancer drug and the nanoparticles or microparticles in tumor blood.

In still another embodiment of the present invention, there is provided a method of treating a solid tumor, comprising the steps of injecting nanoparticles or microparticles to the tumor intravenously and irradiating the tumor with radiation.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A shows the targeted (active) delivery of particles to tumor blood vessels.

FIG. 1B shows the interaction of the particles with laser or ultrasonic radiation.

FIG. 2A shows a laser system for enhancement of drug delivery in solid tumors resulted from hot cavitation and local heating induced by interaction of laser radiation with particles.

FIG. 2B shows an ultrasound system for enhancement of drug delivery in solid tumors resulted from cold cavitation and acoustic streaming induced by interaction of ultrasonic radiation with particles.

FIG. 3A shows interstitial irradiation of a deeply located tumor with particles by laser radiation delivered through an optical fiber inserted in a needle.

FIG. 3B shows laser irradiation of a tumor with particles in a hollow organ via an endoscope.

FIG. 3C shows irradiation of a tumor with particles in a hollow organ by an ultrasonic transducer inserted in the organ.

FIG. 4A shows the penetration due to irradiation by nanosecond Nd:YAG laser pulses.

FIG. 4B shows the penetration due to irradiation by nanosecond Alexandrite laser pulses.

FIG. 4C shows the penetration without laser irradiation (control).

FIG. 6A shows a gross picture of muscle tissue with carbon (left) and graphite (right) particles penetrated in the interstitium due to sonication for 10 minutes.

FIG. 6B shows carbon particle penetration into the tissue due to 10-min. sonication.

FIG. 6C shows a carbon particle penetration into the tissue after 3-min. sonication.

FIG. 6D shows carbon particle penetration in the tissue without sonication.

FIG. 9A shows penetration in the liver tissue due to 10-min. sonication and without sonication.

FIG. 9B shows penetration in the liver, lung, and kidney tissue due to 10-min. sonication.

DETAILED DESCRIPTION OF THE INVENTION

Figure 1A:
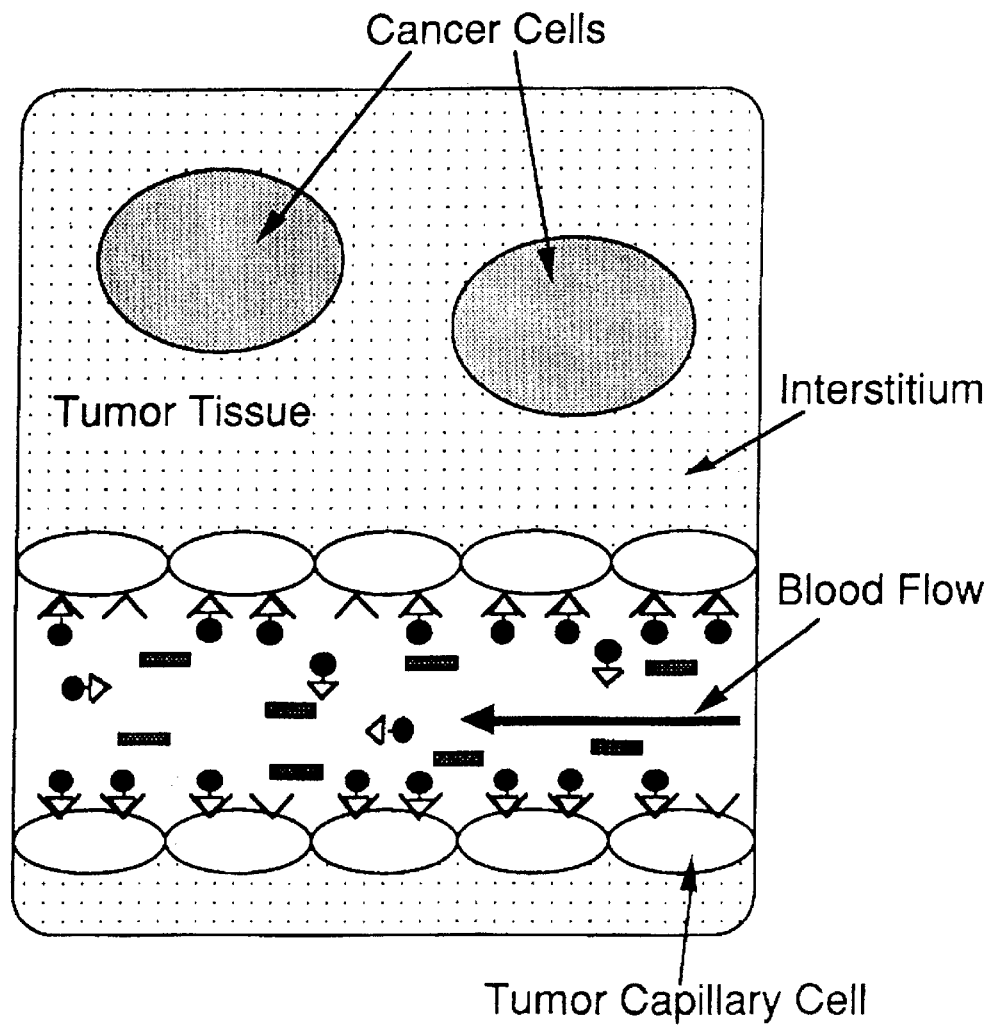
FIGS. 1A–1B.

As used herein, "electromagnetic radiation (wave)" refers to radiation (wave) with electrical and magnetic component which includes (but not limited to) optical (ultraviolet, visible, and infrared light), microwave, and radiofrequency radiation (wave).

As used herein, "ultrasound" or "ultrasonic radiation (wave)" refers to mechanical ("acoustic" or in other terms of "pressure") wave in a medium in the frequency range from 20 kHz to about 1 GHz.

"Nanoparticles" refers generally to particles with a diameter from 0.1 to several hundred of a nanometer. 1 nanometer=$10^{-9}$ meter. "Microparticles" generally refers to particles with a diameter from 0.1 to several hundred of micrometer. 1 micrometer=$10^{-6}$ meter. As used herein, the term "nanoparticles" refers to particles with a diameter from about 0.1 to about 7000 nm.

As used herein, "cavitation" refers to a physical phenomenon in a liquid or a liquid-like medium (including tissue) represented by formation of vapor (or gas) bubbles followed by growth, oscillation, and collapse of the bubbles.

As used herein, "acoustic streaming" refers to a physical phenomenon in a liquid or a liquid-like medium represented by flows of a part of the liquid medium upon irradiation by an ultrasonic wave.

As used herein, "minimal fluence" refers to lowest possible fluence of laser radiation (measured in $J/cm^2$) to induce drug delivery enhancement without damage to normal tissues.

As used herein, "microconvection" refers to micron-sized displacement (flow) in liquid. Generally, convection refers to movement (flow) of a part of a liquid medium.

As used herein, "antibody coating" refers to a coating of a particle due to attachment of a number of antibody molecules to the particle.

As used herein, "particle migration" refers to movement (travel, displacement) of particles. It is cased by cavitation, streaming, or local heating effects.

The purpose of the invention is to disclose means for enhancement of drug delivery through the physiological barriers of solid tumors, such as (1) a tumor blood vessel wall; (2) the interstitium; and (3) a cancer cell membrane. Such methods utilize interaction of electromagnetic or ultrasonic radiation with nanoparticles and microparticles selectively accumulated in tumor blood vessels. The interaction alters the physiological properties of the barriers of solid tumors due to: (1) cavitation induced by ultrasonic, pulsed laser, or microwave radiation near the particles; (2) transient local heating of the particles by laser or microwave radiation; and (3) acoustic streaming near the particles. The physical forces result in rupture of tumor blood vessel wall and cancer cell membrane, and microconvection in the interstitium leading to enhanced delivery of the macromolecular drugs into cancer cells.

Nanoparticles or microparticles having certain physical properties and capable of inducing cavitation, local heating, or acoustic streaming upon irradiation by electromagnetic or ultrasonic radiation are intravenously injected and selectively accumulated in tumor vasculature. Passive or active delivery of long-circulating particles provides a selective accumulation of the particles in tumor vasculature. The particles are coated with polyethylene glycol or polyethylene oxide to provide long circulation in blood. Recently discovered antibodies and short peptide sequences can be used for active delivery of the particles to tumor blood vessels. Experiments on animal models demonstrated the feasibility of active delivery of long-circulating nanoparticles loaded with anti-cancer drugs and coated with antibodies that results in their selective accumulation in tumors.

Cavitation (formation, growth, oscillations, and collapse of microbubbles) is initiated by the nano- or microparticles when ultrasonic or electromagnetic radiation is applied. A source of radiation is placed on the surface of skin or inserted in a hollow organ or in the interstitium so that the irradiation of the particles in the tumor is provided.

Cavitation is known as both "cold" cavitation, induced by tensile (negative) pressure of ultrasonic waves and "hot" cavitation, induced by evaporation upon heating of an absorbing medium by electromagnetic radiation. Ultrasonic irradiation results in cavitation near the particles which serves as cavitation nuclei significantly reducing cavitation threshold. The material, structure, and dimensions of the particles and ultrasound frequency are specially selected to provide cavitation effects at minimal power of the ultrasonic wave.

Pulsed electromagnetic (laser or microwave) irradiation results in evaporation of blood near the particles strongly absorbing optical or microwave radiation. The material, structure, and dimensions of the particles as well as radiation wavelength and pulse duration are specially selected to provide cavitation effects at minimal fluence of laser or microwave radiation. This yields cavitation confined within the tumor and with minimal mechanical or thermal damage to normal tissues.

Perforation of tumor blood vessel walls is induced by the growing, oscillating, and collapsing cavitation bubbles. As a result, anti-cancer drugs circulating in blood penetrate through the tumor blood vessel wall into the interstitium. The cavitation bubbles also induce microconvection in the interstitium. Anti-cancer drugs migrate in the interstitium due to microconvection. Perforation of cell membrane is induced by the cavitation bubbles, which allows the anti-cancer drugs to penetrate from the interstitium into the cancer cells. Therefore, the death of cancer cells in the tumor is caused by chemical or biological effects of anti-cancer drugs; mechanical or thermal damage to the cancer cells from cavitation bubbles; and mechanical or thermal damage as well as chemical and biological damage to the tumor vasculature from cavitation bubbles and the drugs.

In one embodiment of the present invention, there is provided a method of enhancing anti-cancer drug delivery in a solid tumor, comprising the steps of administrating at least one anti-cancer drug to the tumor; injecting nanoparticles or microparticles to the tumor intravenously; and irradiating the tumor with radiation.

Generally, the anti-cancer drug is selected from the group consisting of a monoclonal antibody, a cytokine, an antisense oligonucleotide, a gene-targeting vector and any other macromolecular therapeutic agent. Generally, the tumor occurs in the organ selected from the group consisting of breast, lung, brain, liver, skin, kidney, GI organ, prostate, bladder, gynecological organ and any other hollow organ.

Preferably, the nanoparticles or microparticles are long circulating particles with or without antibody coating, wherein the antibody is directed against tumor vasculature. The nanoparticles or microparticles can be metal particles, carbon particles, graphite particles, polymer particles loaded with an absorbing dye, liquid particles loaded with an absorbing dye or porous particles having gas-filled pores. The nanoparticle has a diameter from about 0.1 n m to about 7000 nm.

Preferably, the radiation is optical pulsed radiation generated from a laser or non-laser source. Specifically, the optical radiation is in the spectral range from 0.2 $\mu$m to 2 $\mu$m and delivered through the skin surface or via optical fibers inserted in a needle or endoscopes to the tumor.

Preferably, the radiation is ultrasonic radiation generated from an ultrasonic transducer. Specifically, the ultrasonic radiation is in the frequency range from 20 to 500 kHz and delivered through the skin surface to the tumor.

In another embodiment of the present invention, there is provided a system for enhancement of anti-cancer drug delivery in a solid tumor, comprising a source of radiation; an electronic system or means for monitoring of the radiation; a system for delivery of the radiation to the tumor; nanoparticles or microparticles absorbing the radiation; an injection system or means for administration of the anti-cancer drug and the nanoparticles or microparticles in tumor blood.

In still another embodiment of the present invention, there is provided a method of treating a solid tumor without anti-cancer drugs, comprising the steps of injecting nanoparticles or microparticles to the tumor intravenously and irradiating the tumor with radiation.

The following examples are given for the purpose of illustrating various embodiments of the invention and are not meant to limit the present invention in any fashion.

EXAMPLE 1

Short Laser Pulses

It is known that severe local heating of strongly absorbing particles in transparent optical materials produces vapor microbubbles upon irradiation by short laser pulses, which results in mechanical and thermal damage to the materials. Local heating of a strongly absorbing particle in a medium can be induced, if laser pulse duration is shorter than the time of heat diffusion. The heat diffusion time, $\tau$, is estimated as $\tau \sim d^2/k\chi$, where d is the dimension of the particle, k is a coefficient which is dependent on the shape of the particle, and $\chi$ is the thermal diffusivity of the medium. For example, local temperature rise above 20,000° K can be achieved in laser glass containing a metal particle with the radius of 200 nm and absorption coefficient of about $10^6$ cm$^{-1}$ upon irradiation with nanosecond laser pulses with the fluence of 20 J/cm$^2$.

Local heating of exogenous strongly absorbing nanoparticles by short (nanosecond) and ultrashort (picosecond) laser pulses results in explosive evaporation of blood in tumor vasculature and formation of microbubbles.

EXAMPLE 2

Active and Passive Delivery

Figure 1B:
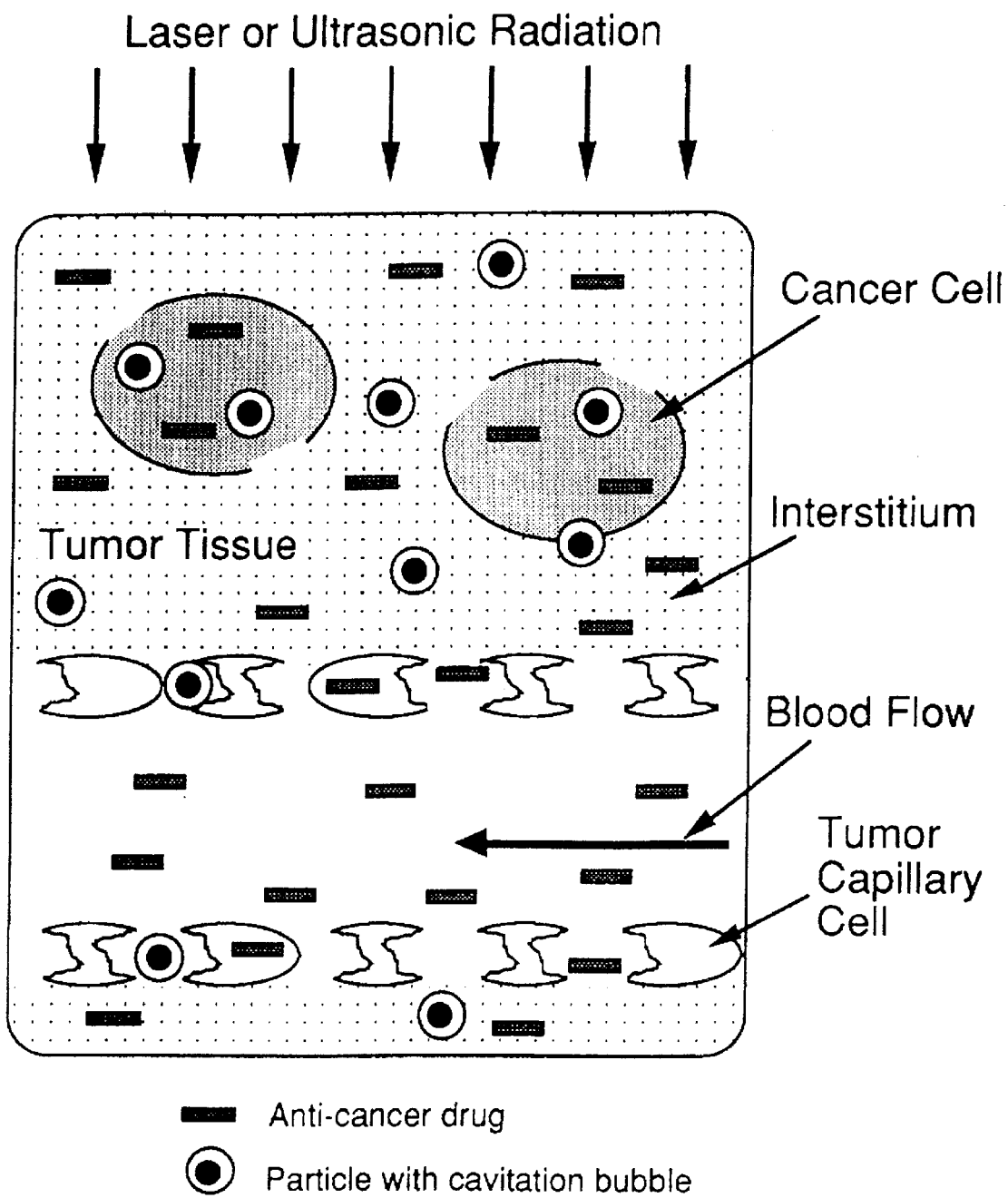

To avoid rapid clearance by the reticuloendothelial system and obtain selective accumulation in tumors, long-circulating particles coated with a surfactant (polyethylene glycol or polyethylene oxide) are used. The long-circulating particles are attached to antibodies directed against antigens in tumor vasculature, which results in selective delivery of the particles to tumor blood vessel walls (active delivery) (see FIG. 1A). Short peptide sequences for organ specific targeting may be used for this purpose. The long-circulating particles without antibodies also selectively accumulate in tumors because of leakage through tumor vasculature (passive delivery). FIG. 1B shows the interaction of the particles with pulsed laser or ultrasonic radiation. Cavitation induced by laser or ultrasonic radiation results in perforation of tumor blood vessels and penetration of the particles and anti-cancer drug into the interstitium due to microconvection. The cavitation-induced microconvection provides delivery of the particles and anti-cancer drug through the interstitium to cancer cell membranes. Perforation of the cell membranes allows the drug molecules to penetrate into the cancer cells.

EXAMPLE 3
Systems for Enhancing Drug Delivery in Solid Tumors

Figure 2A:
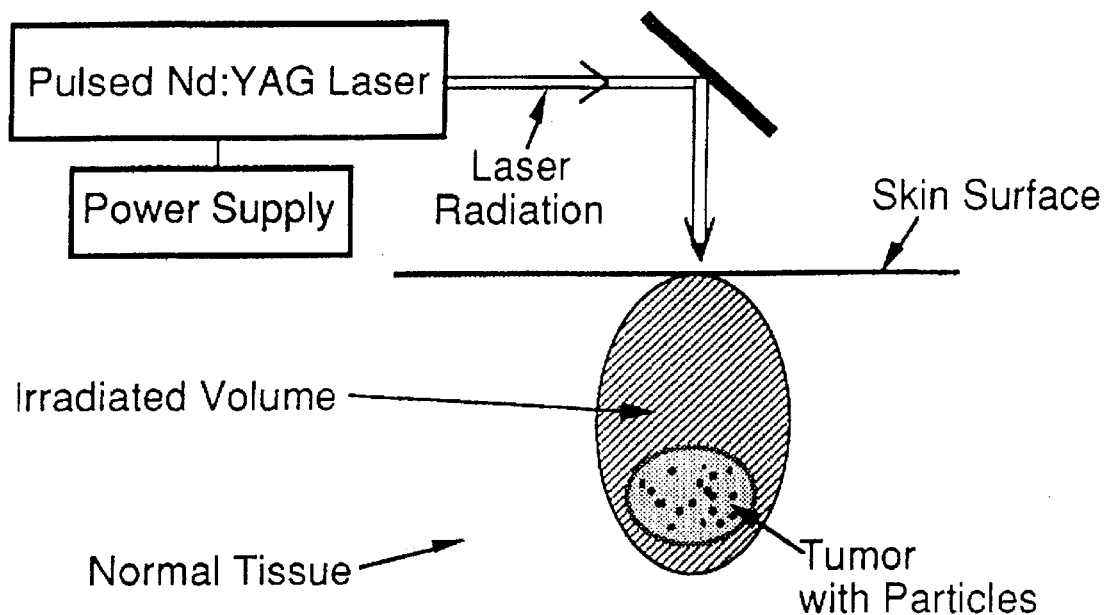
FIGS. 2A–2B.

A laser system for the enhancement of drug delivery in solid tumors was developed (see FIG. 2A). The system utilizes nanosecond Nd:YAG laser radiation with the wavelength of 1064 nm to induce local heating of strongly absorbing particles. The system consists of: (1) Nd:YAG laser with electronic system for monitoring of radiation parameters (pulse energy and duration, number of pulses, repetition rate, power); (2) a fiber-optic system or conventional optical system for delivery of laser radiation through the skin to the tumor; (3) nano- or microparticles strongly absorbing laser radiation and attached to antibodies directed against tumor vasculature; and (4) an injection system for administration of the particles and anti-cancer drugs in blood.

Figure 2B:
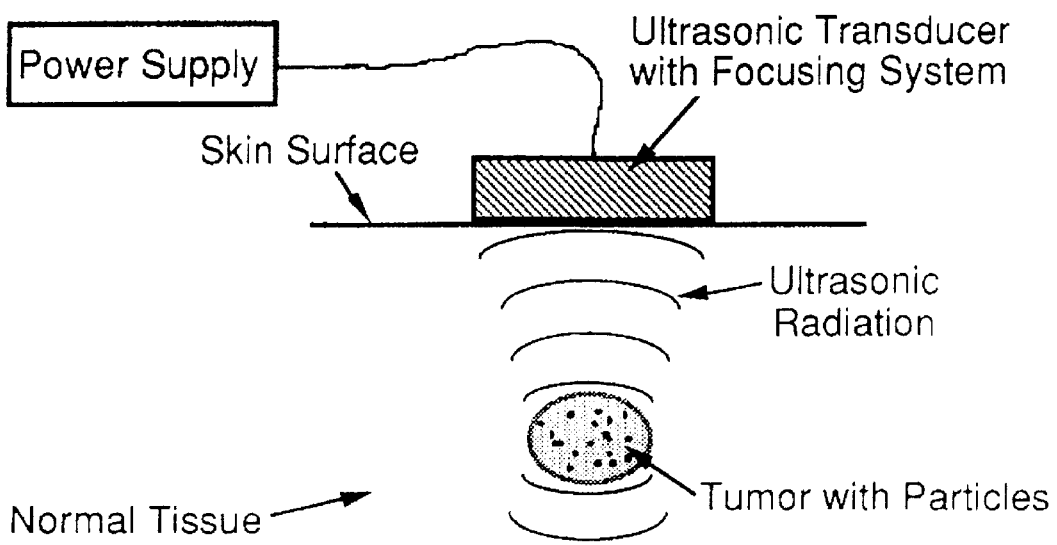

An ultrasound system for the drug delivery enhancement utilizing ultrasonic waves capable of inducing cavitation in blood and tissues was also developed (see FIG. 2B). The system consists of: (1) ultrasonic transducer (or transducer array) for producing ultrasonic wave with a frequency in the range from 20 kHz to 10 MHz; (2) an electronic system for providing power supply for the ultrasonic transducer and monitoring of radiation parameters (pressure amplitude, frequency, pulse duration, number of pulses, repetition rate, ultrasonic power); (3) a focusing system for directing and focusing ultrasonic radiation to tumors; (4) nano- or microparticles decreasing threshold of cavitation upon irradiation by the ultrasonic radiation and attached to antibodies directed against tumor vasculature; and (5) an injection system for administration of the particles and anti-cancer drugs in blood.

EXAMPLE 4
Interstitial Irradiation of Tumors

Figure 3A:
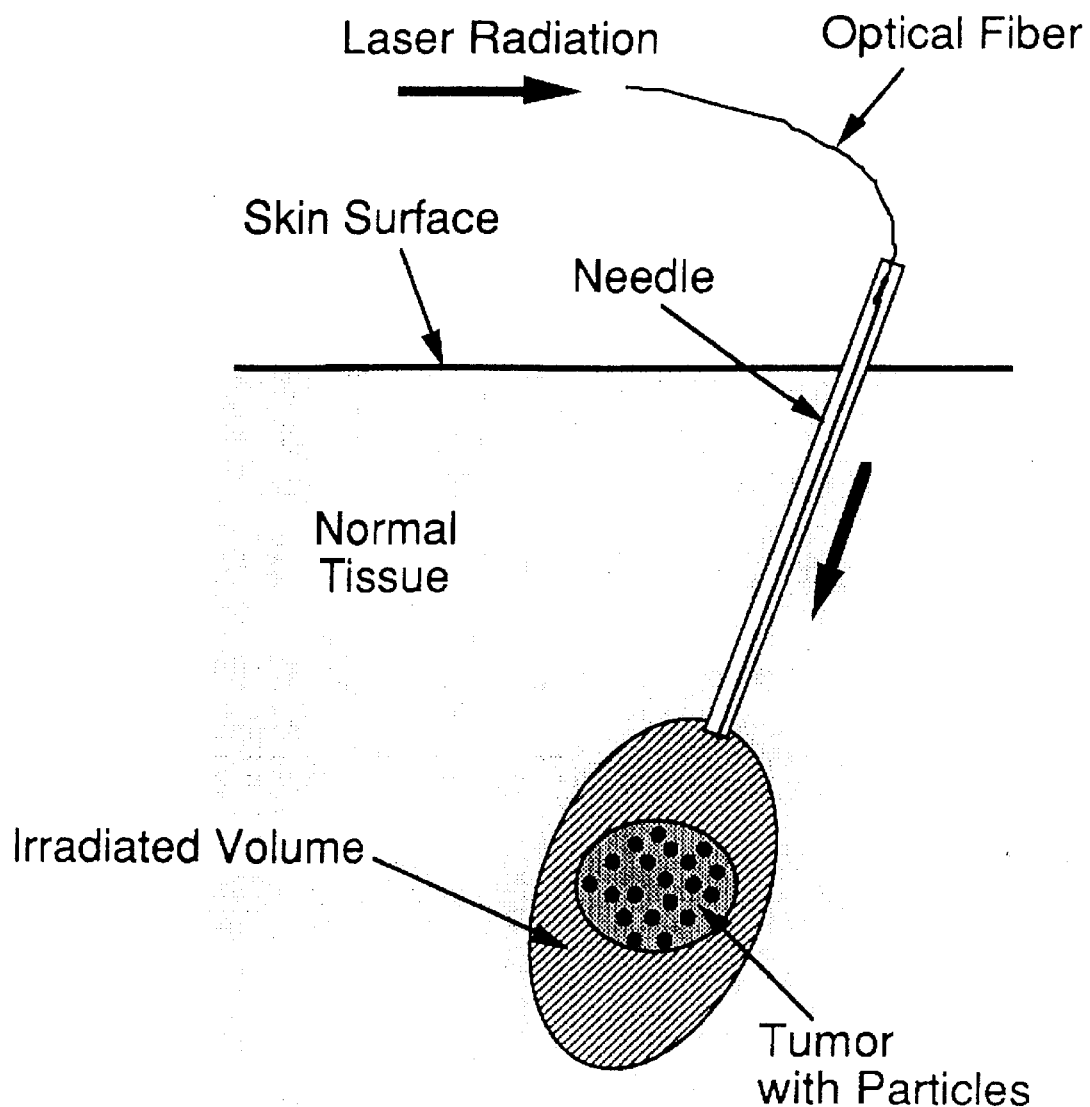
FIGS. 3A–3C.

Near infra-red radiation with sufficient fluence can penetrate only up to approximately 2–4 cm into tissues depending on their optical properties. To overcome this problem, optical fibers inserted into needles can be used for irradiation of deeply located tumors (so-called interstitial irradiation of tumors). FIG. 3A illustrates a laser system utilizing the interstitial irradiation of tumors. An optical fiber inserted into a needle is introduced into a tumor and laser radiation is not attenuated by tissues between the tumor and skin surface. This provides laser irradiation of the tumor with the fluence sufficient to enhance drug delivery.

Figure 3B:
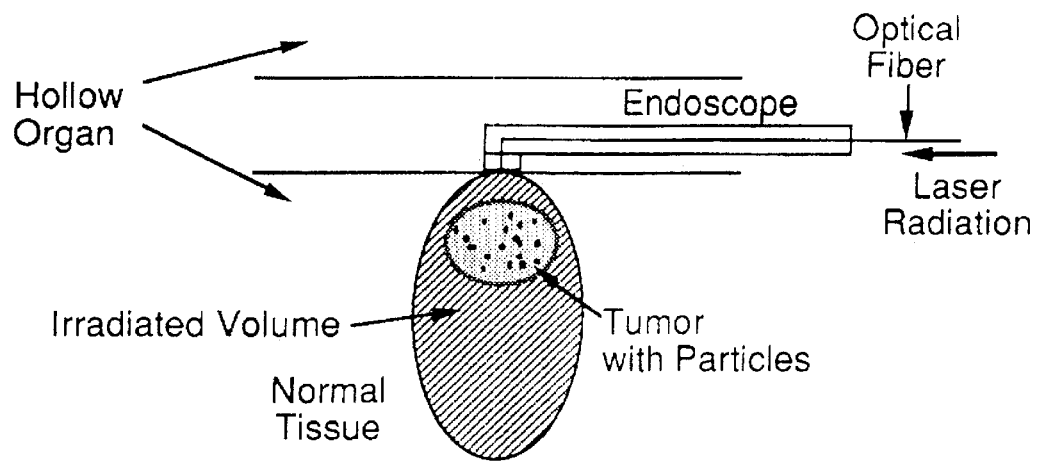

A laser system utilizing irradiation of tumors in the lung, stomach, intestine, and other hollow organs through optical fibers or endoscopes is shown in FIG. 3B. Near infra-red, visible, or near-UV laser radiation is used in this case because the tumors are irradiated directly and without attenuation in the skin and normal tissues.

Figure 3C:
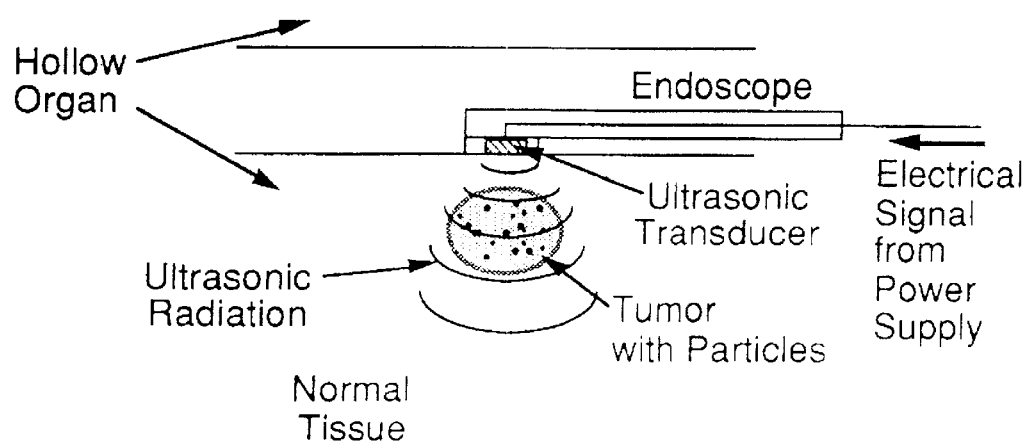

FIG. 3C illustrates an ultrasound system utilizing transducer incorporated in an endoscope for irradiation of tumors in hollow organs. The tumor is directly irradiated by the transducer that allows more efficient drug delivery. The systems shown in the FIGS. 3A, 3B and 3C provide selective irradiation of solid tumors at lower incident laser pulse energy and ultrasonic power that minimizes damage to normal tissues.

Figure 4A:
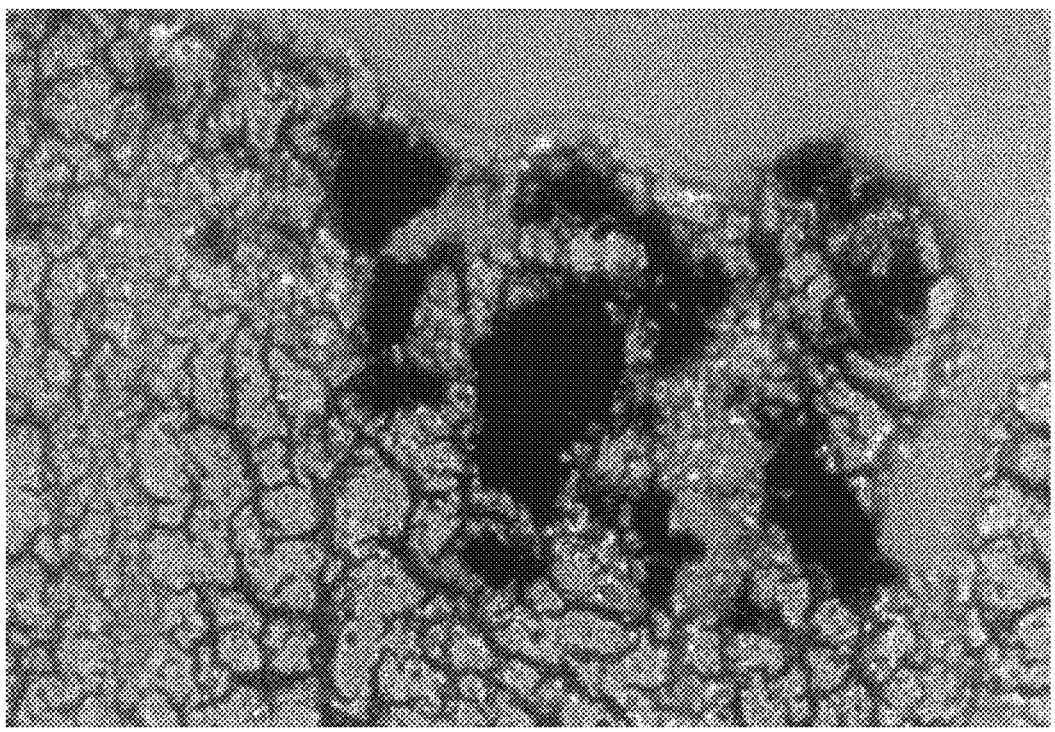
FIGS. 4A–4C show particle penetration in rat liver tissue.

EXAMPLE 5
Laser Irradiation-Induced Particle Penetration in Rat Liver Tissue Freshly excised ex vivo rat liver was used. Activated carbon particles with the diameter of 1 μm were used as particles strongly absorbing Nd:YAG laser radiation with the wavelength of 1064 nm. The particles were placed between two liver slabs with the dimensions of 10×10 mm. The thickness of each slab was 3 mm. The slabs were irradiated for 10 minutes by the laser pulses with the energy of 90 mJ, duration of 15 ns, repetition rate of 10 Hz. The laser spot diameter was 8 mm yielding incident fluence of 0.18 J/cm$^2$. The slabs were placed in 1% water solution of fluorescein isothiocyanate-dextran (FITC-Dextran) to study penetration of macromolecules in the liver tissue. Molecular weight of the FITC-dextran is 12,000. After irradiation the slabs were rinsed in pure water to remove the particles and dextran from the tissue surface. Laser-induced explosive evaporation of water results in penetration and migration of the particles and dextran in the interstitium (see FIG. 4A). The black spots represent clusters of the carbon particles. Magnification is ×350. Particle penetration is up to 160 μm.

Figure 4B:
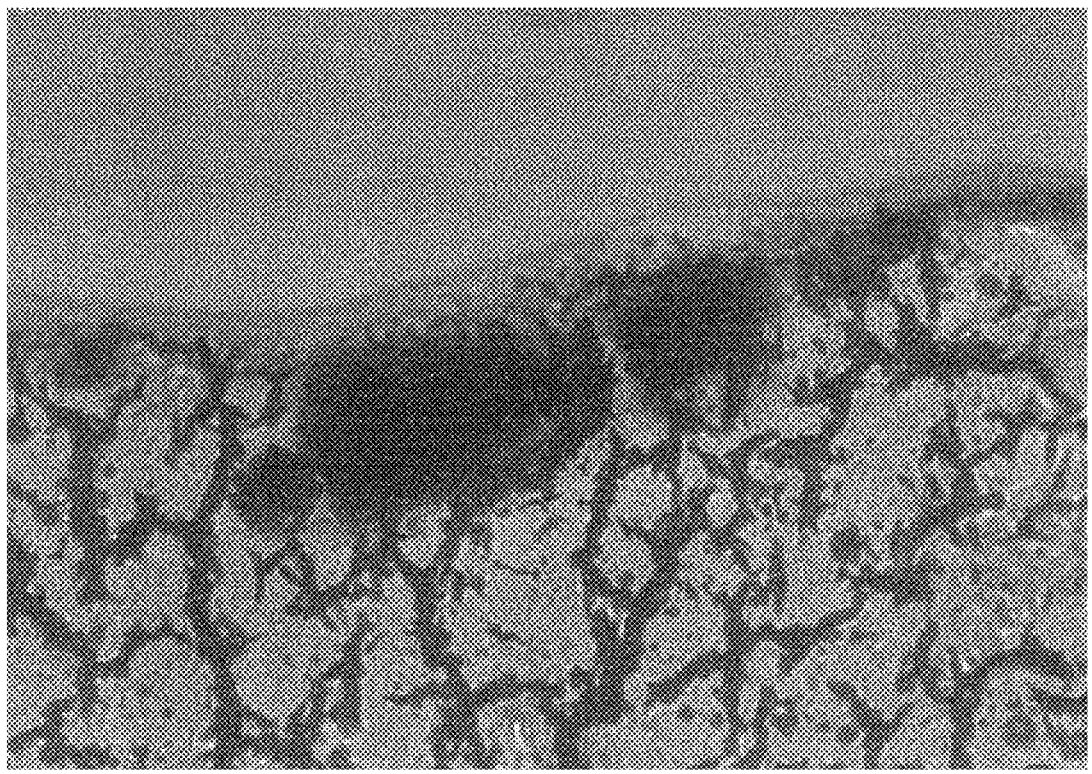

Particle penetration in the rat liver tissue due to irradiation by nanosecond Alexandrite laser pulses with the wavelength of 720 nm was also studied (FIG. 4B). The liver slabs were irradiated for 10 minutes by the laser pulses with the energy of 90 mJ, duration of 160 ns, repetition rate of 2 Hz. All other conditions are the same as in the case of Nd:YAG irradiation. The laser spot diameter was 4 mm yielding incident fluence of 0.72 J/cm$^2$. Magnification is ×460. Particle penetration is up to 60 μm.

Figure 4C:
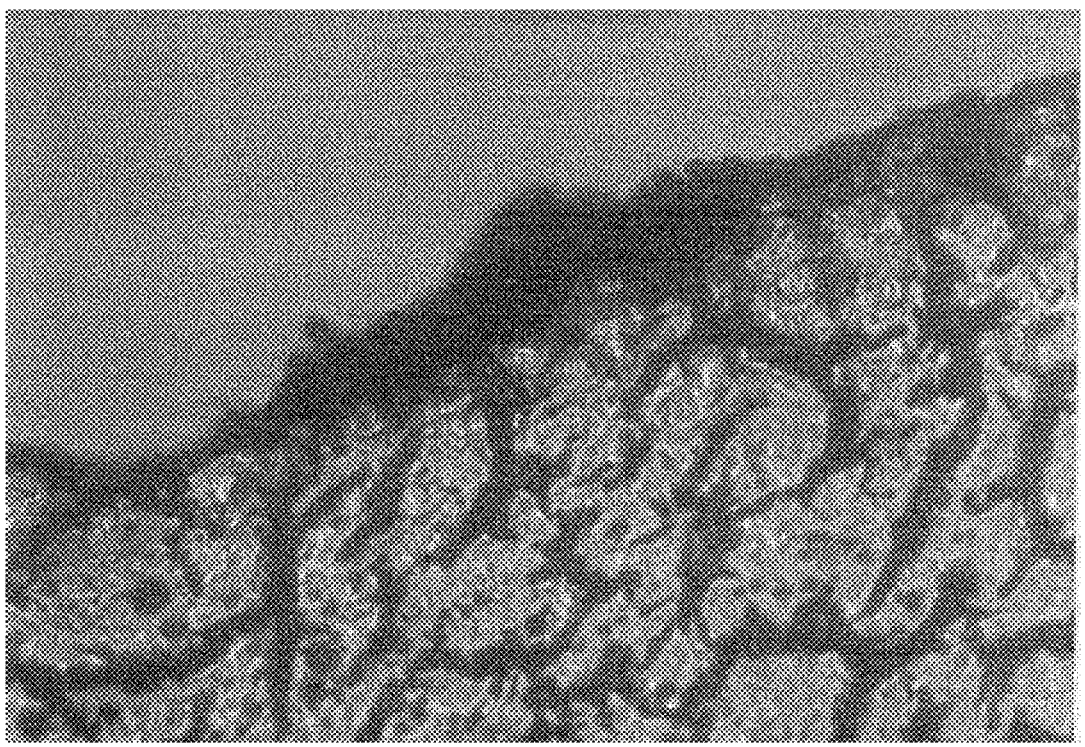

As in a sample without application of laser irradiation (control), some particles are visible only on the tissue surface (FIG. 4C). However, the particles can not penetrate into the interstitium. Magnification is ×460.

Figure 5:
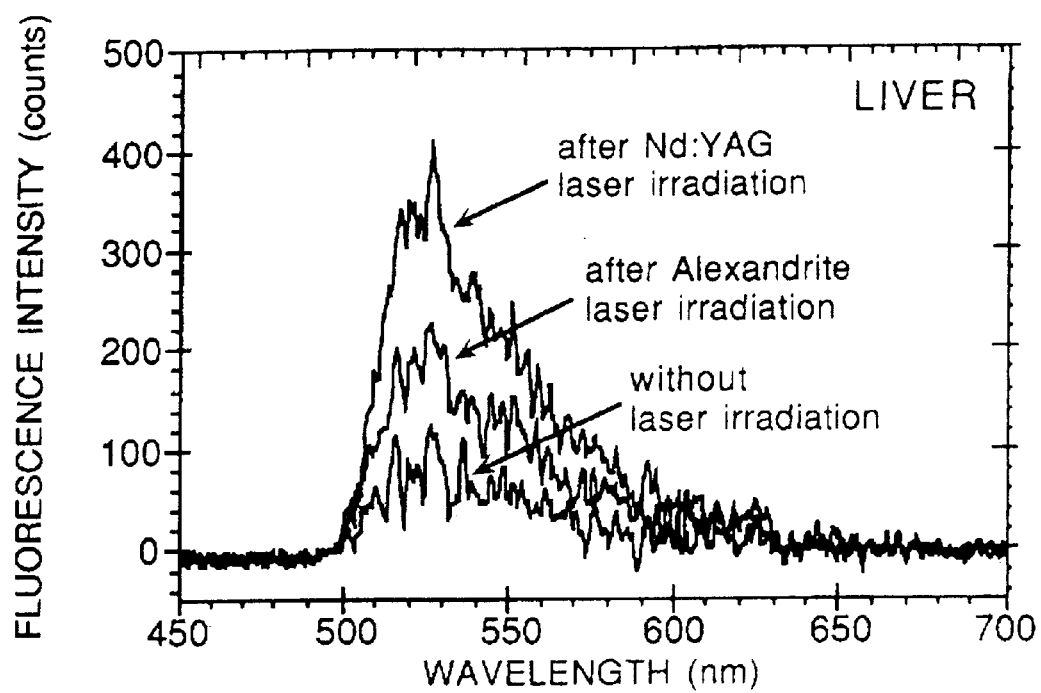
FIG. 5 shows fluorescence spectra of fluorescein isothiocyanate-dextran (FITC-Dextran) penetrated into the liver tissue due to irradiation by nanosecond Nd:YAG laser pulses (upper spectrum), Alexandrite laser pulses (middle spectrum) and without laser irradiation (lower spectrum).

Fluorescence spectra of FITC-Dextran penetrated in the liver tissue was further studied (FIG. 5). All conditions are the same as described in the FIG. 4. The wavelength for the fluorescence excitation is 400 nm. Increased penetration of the dextran molecules is obtained upon Nd:YAG laser irradiation (4-fold in comparison with the non-irradiated sample). Dextran penetration upon Alexandrite laser irradiation is also noticeable (2-fold in comparison with the non-irradiated sample).

These data demonstrate that interaction of pulsed laser radiation with strongly absorbing particles results in penetration of the particles and macromolecules into the interstitium and migration of the particles and macromolecules in the interstitium.

Figure 6A:
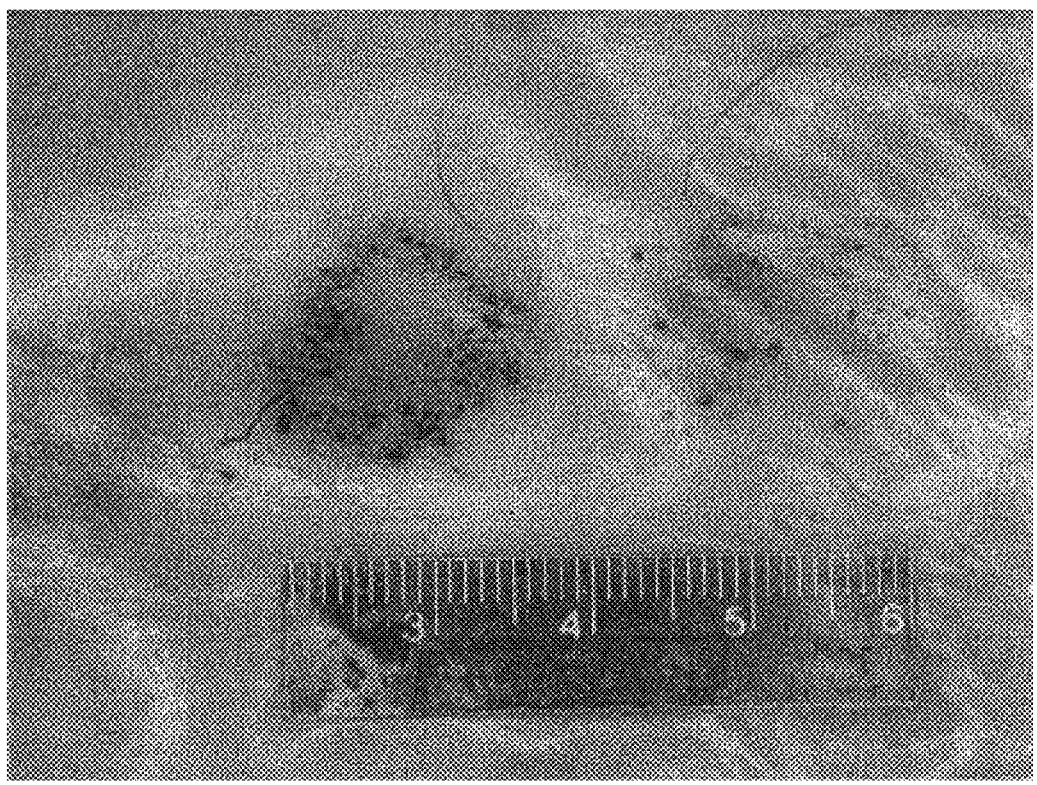
FIGS. 6A–6D.
Figure 6B:
Figure 6C:
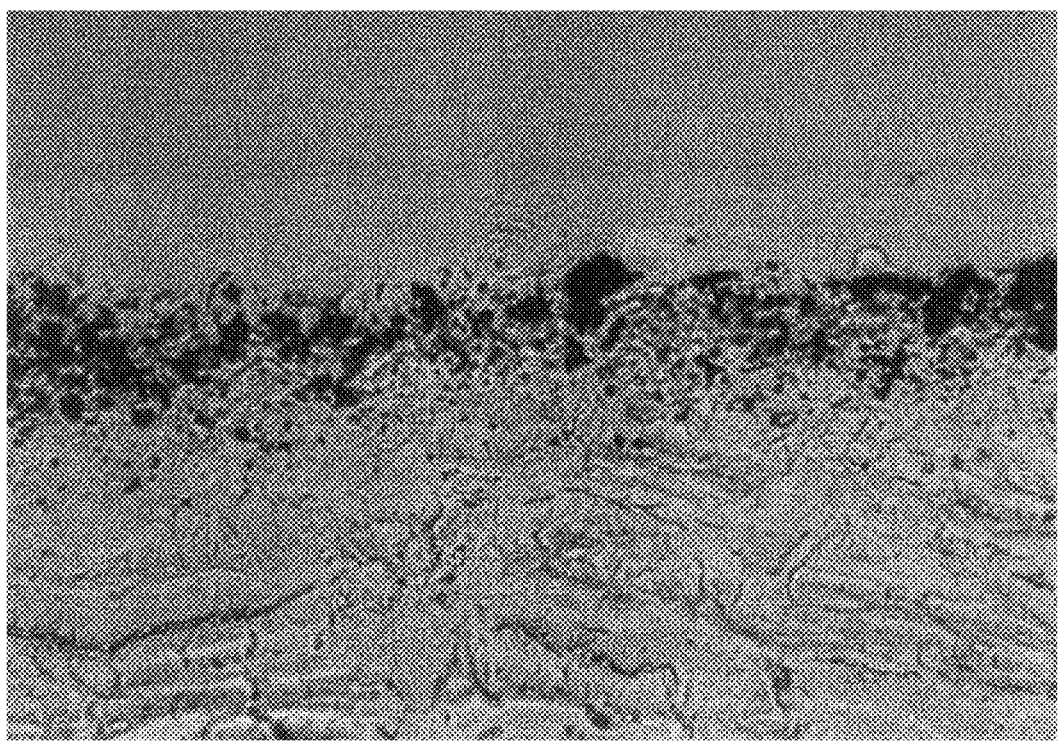

EXAMPLE 6
Sonication-Induced Particle Penetration in Chicken Muscle Tissue Particle penetration due to sonication was conducted in chicken muscle tissue (FIGS. 6A, 6B and 6C). FIG. 6A shows a gross picture of chicken muscle tissue with carbon (left) and graphite (right) particles penetrated in the interstitium due to sonication for 10 minutes. The activated carbon and graphite particles with the diameter of 1–2 μm were used as cavitation nuclei. The activated carbon particles have numerous pores filled with air that substantially decrease the cavitation threshold and enhances cavitation. Ultrasonic radiation with the frequency of 50 kHz and incident intensity of 250 mW/cm$^2$ was employed for the experiments. Penetration of the activated carbon particles is more pronounced. No cavitation was visible on the tissue surface where the particles were not applied.

Figure 6D:
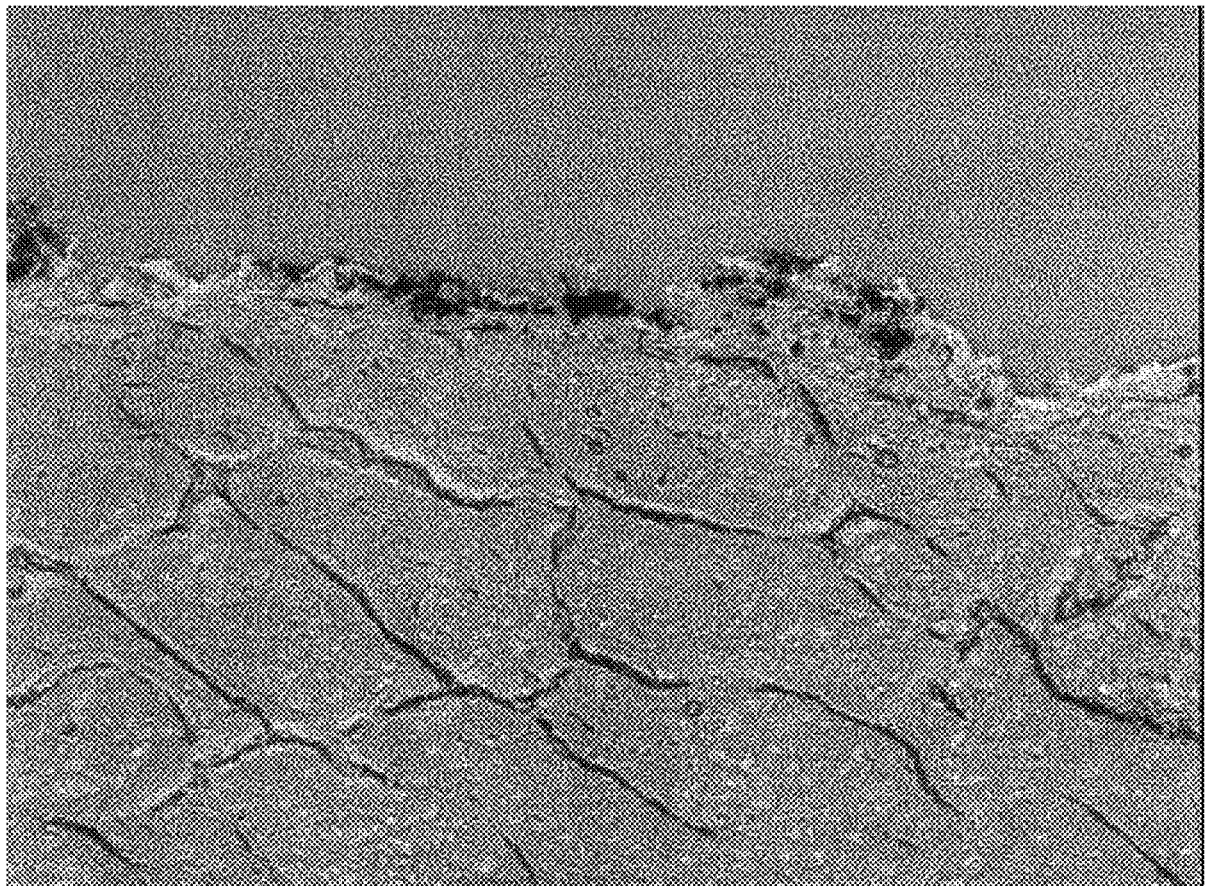

Also shown is that carbon particle penetrates into the tissue up to 180 μm due to 10 minute sonication (FIG. 6B, Magnification: ×230) and up to 60 μm due to 3 minute sonication (FIG. 6C, Magnification: ×300). Particles are visible only on the tissue surface without penetrating into the interstitium when no sonication was applied (FIG. 6D, Magnification: ×340).

Figure 7:
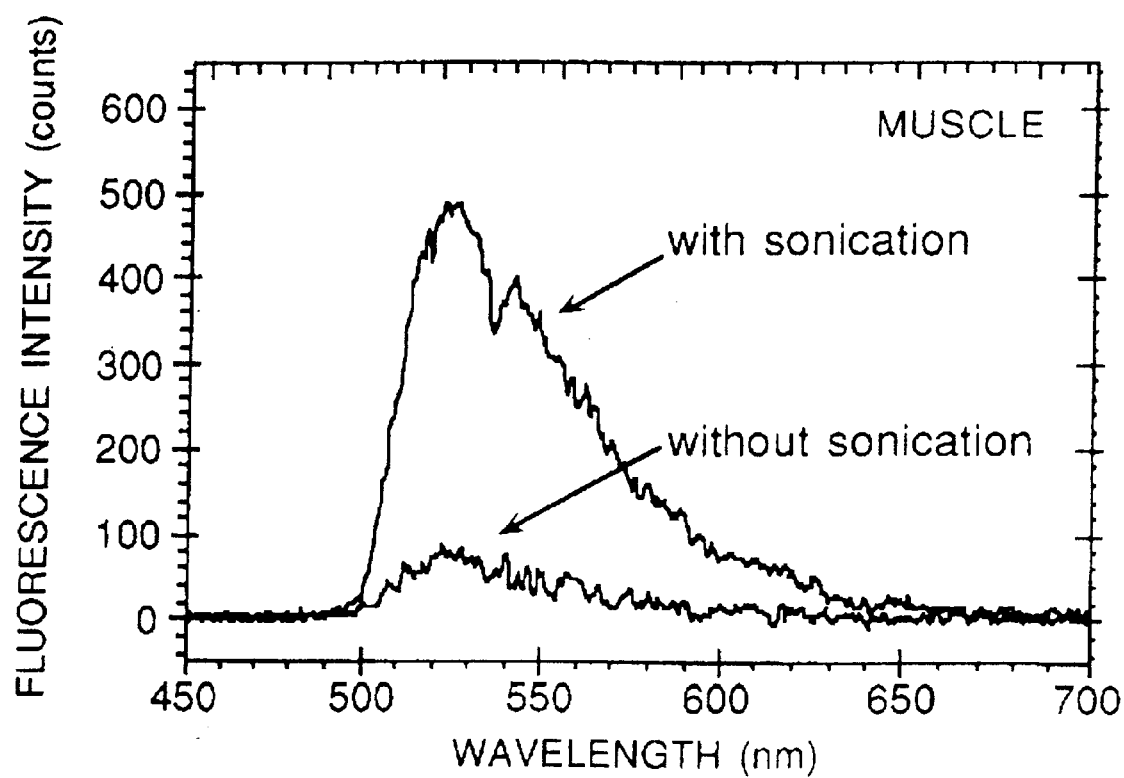
FIG. 7 shows a fluorescence spectra of FITC-Dextran penetrated in the muscle tissue due to 10-min. sonication and without sonication.

Fluorescence spectra of FITC-Dextran penetrated in the muscle tissue due to 10-min. sonication and without sonication was also conducted (FIG. 7). All conditions are the same as in the FIG. 6. The data demonstrate more than 6-fold increase of the penetration of the macromolecules into the tissue which is caused by ultrasound-induced cavitation. The cavitation results in microconvection in the tissue leading to enhanced delivery of macromolecules in the interstitium.

EXAMPLE 7

Sonication-Induced Particle Penetration in Rat Tissues

Figure 8A:
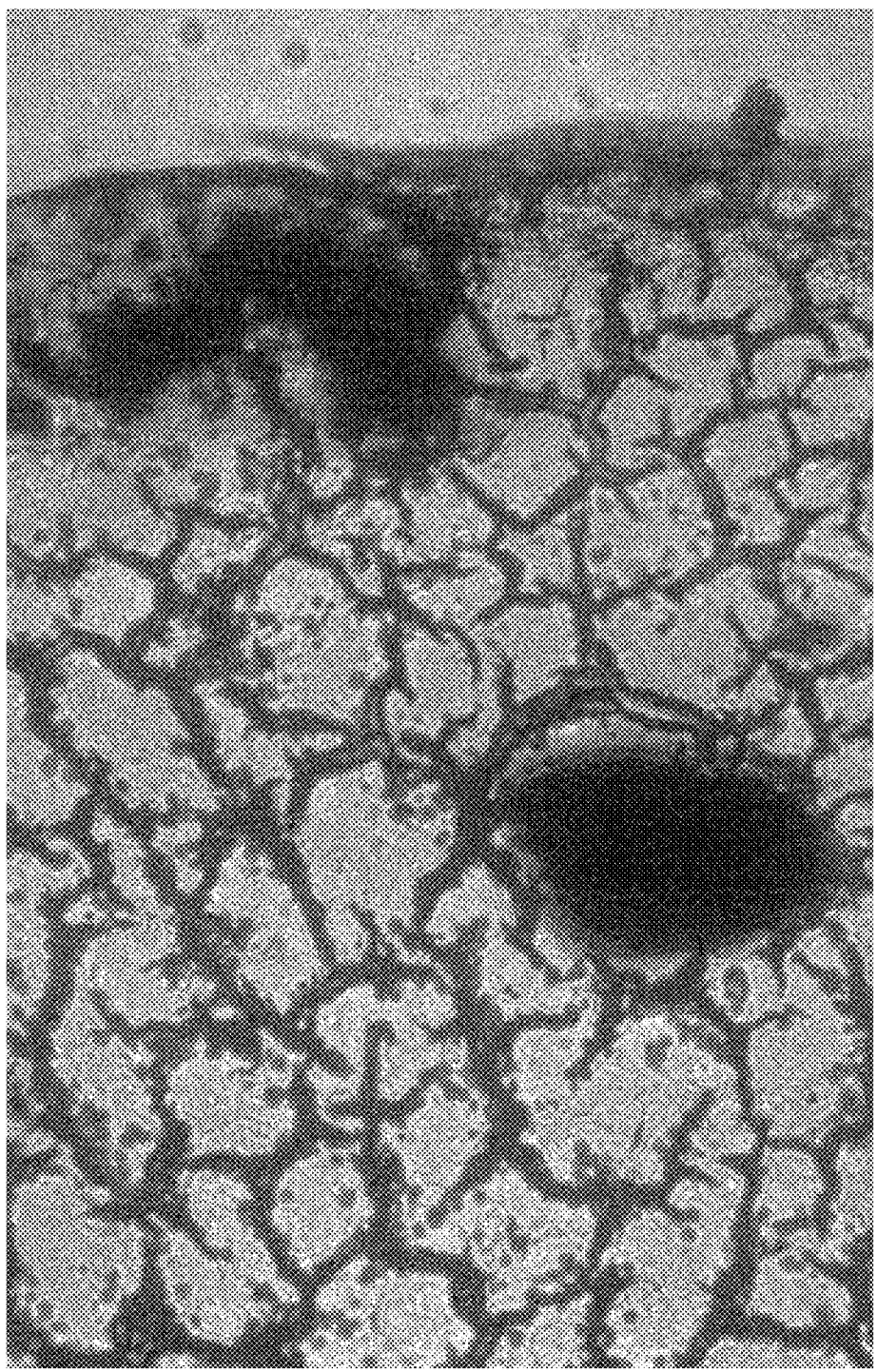
FIGS. 8A–8C show particle penetration due to 10-min. sonication in liver (FIG. 8A), kidney (FIG. 8B) and lung tissues (FIG. 8C).
Figure 8B:
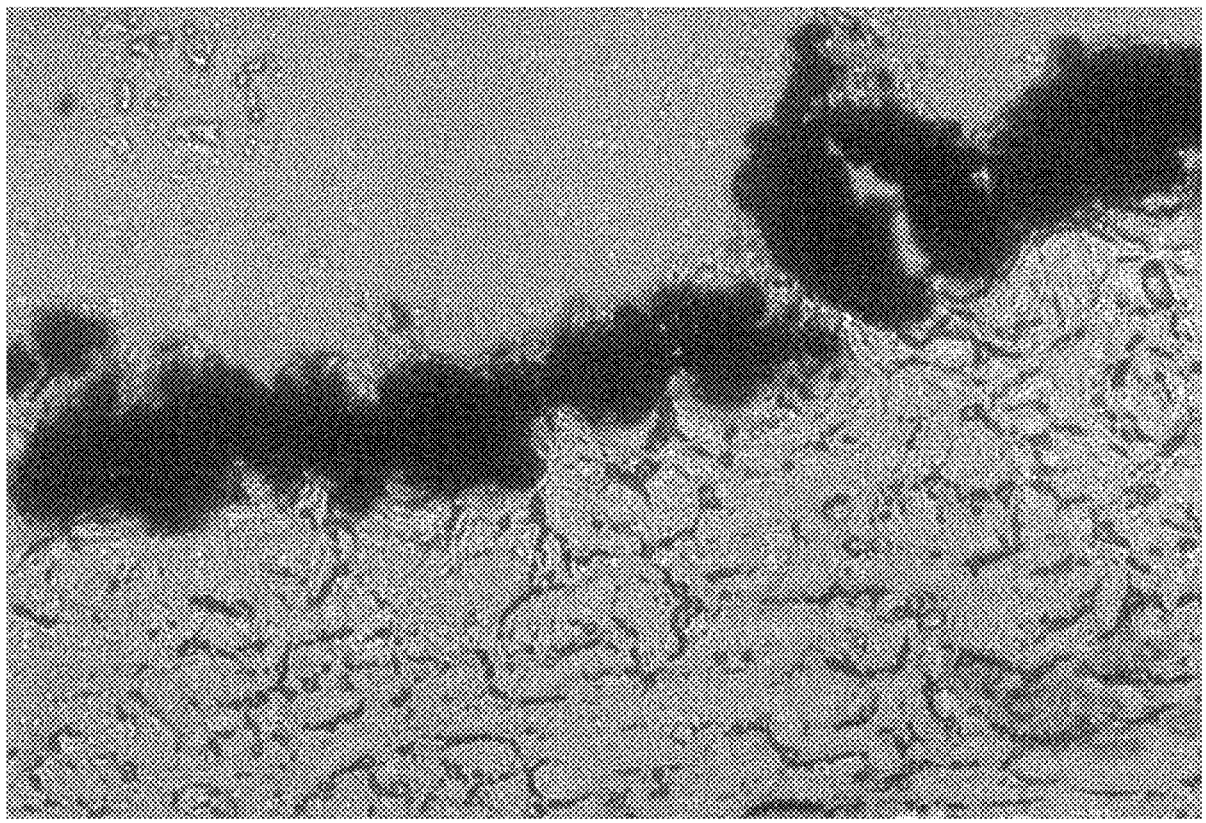
Figure 8C:
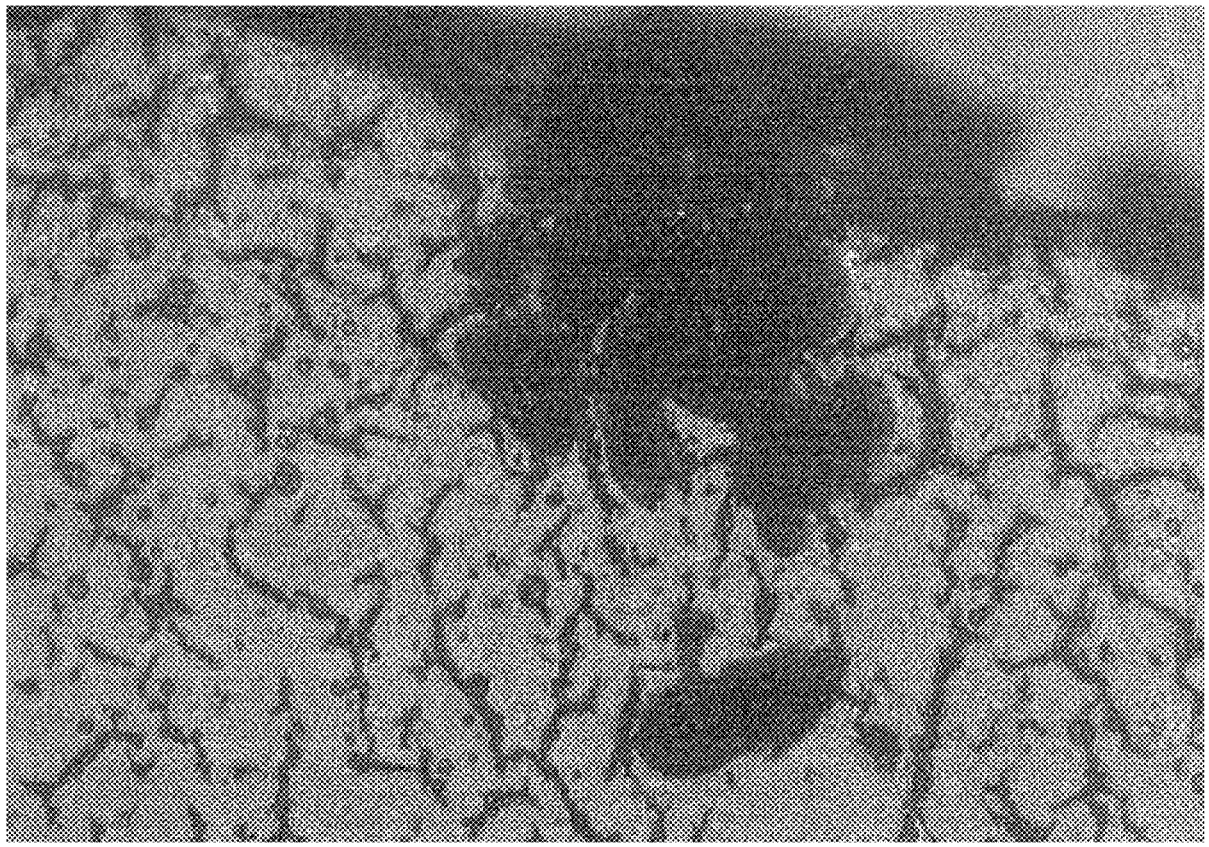

Particle penetration due to 10 minute sonication was studied in freshly excised rat tissues ex vivo (FIGS. 8A, 8B and 8C, Magnification: ×460). The penetration is up to 160 $\mu$m in the liver, up to 30 $\mu$m in the kidney, and up to 150 $\mu$m in the lung tissue.

Figure 9A:
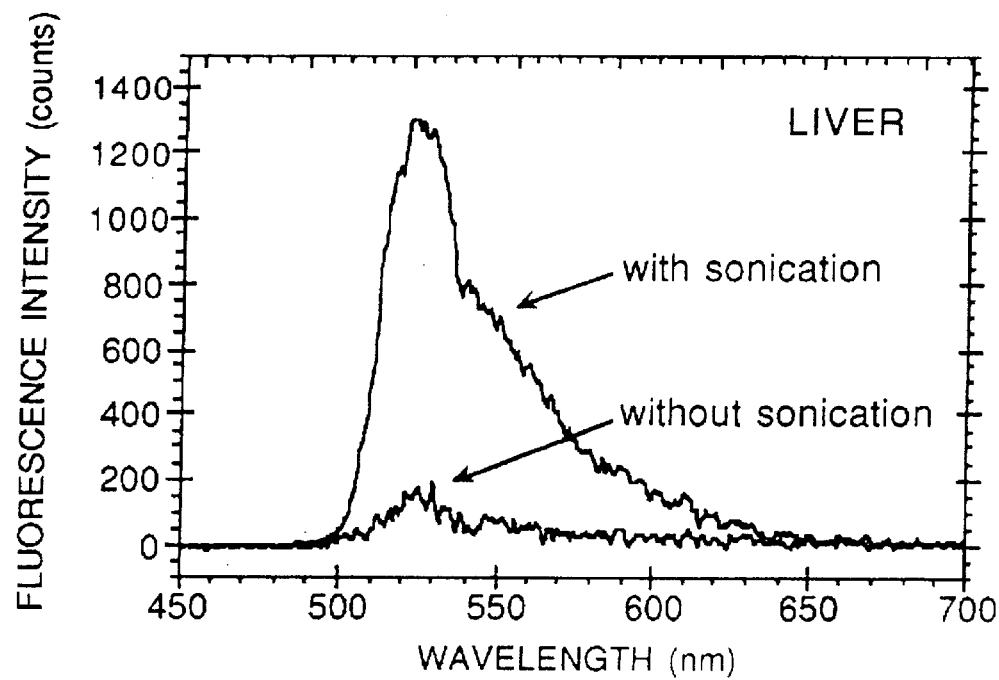
FIGS. 9A–9B show fluorescence spectra of FITC-Dextran.
Figure 9B:
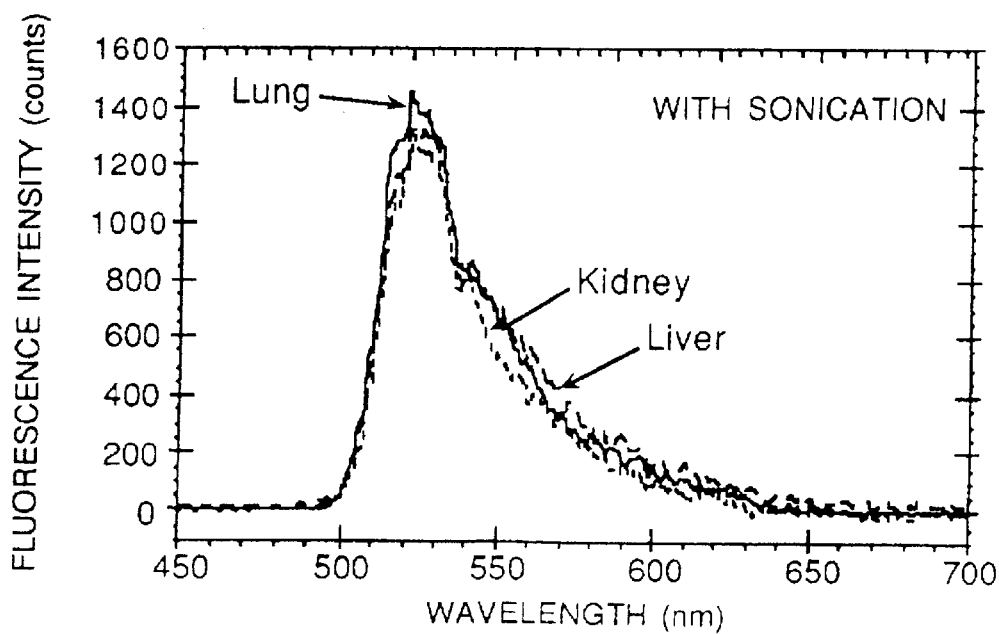

Fluorescence spectra of FITC-Dextran penetrated in the rat liver tissue due to 10-min. sonication and without sonication was further conducted (FIG. 9A). The intensity of fluorescence from the sonicated tissue is greater 6.7 times than the one from the non-sonicated. FIG. 9B shows fluorescence spectra from liver, lung, and kidney tissue after 10-min. sonication. The intake of the dextran molecules is almost the same for all the tissues. The ultrasound data demonstrate that the interaction of the particles with ultrasonic radiation induces cavitation in tissues and the cavitation results in penetration of particles and macromolecules into the interstitium.

Discussion

The present invention utilizes the interaction of laser or ultrasonic radiation with exogenous intravenously injected particles for the purpose of enhancing drug delivery in solid tumors. The interaction enhances penetration of anti-cancer drugs, especially macromolecular therapeutic agents, from blood into cancer cells preferably due to cavitation accompanied by disruption of tumor blood vessel walls and cancer cell membranes as well as microconvection in the interstitium.

Local heating of exogenous strongly absorbing nanoparticles by short (nanosecond) and ultrashort (picosecond) laser pulses results in explosive evaporation of blood in tumor vasculature and formation of microbubbles. Optical radiation in the near infra-red and visible spectral range (so-called "therapeutic window": $\lambda$=600–1300 nm) has low attenuation in tissues. Therefore, it can induce local heating of the strongly absorbing particles in deeply located tumors without damage to irradiated tissue surface. For example, absorption and scattering coefficients of breast tissue equal to 0.05–0.08 $cm^{-1}$ and 5.0–9.0 $cm^{-1}$, respectively, in the near infra-red spectral range. Using these values, one can estimate that the fluence of $10^{-1}$–$10^{-2}$ $J/cm^2$ can be achieved at the depth of 2–3 cm, if breast tissue is irradiated by the nanosecond Nd:YAG laser with a pulse energy of 1 J and a beam diameter of 1 cm. Since temperature rise is proportional to fluence, local transient temperature of about 50–140° C. can be obtained near the particles.

Overheating of water above 100° C. near absorbing particles induces local explosive microevaporation resulting in pressure rise, bubble formation, and outward momentum. Collapse of the microbubbles induces strong inward momentum and pressure transients. Both the explosive evaporation and the following bubble collapse perforate tumor vasculature and therefore increase vascular permeability, which allows therapeutic agents to penetrate from blood into the interstitium, migrate in the interstitium, and penetrate into the cancer cells. Moderate heating without evaporation can induce local thermal damage or local temperature rise without damage which may also increase vascular permeability. Pulsed laser heating of absorbing volumes generates thermoelastic pressure transients in tissues which may contribute to damaging tumor vasculature or increasing vascular permeability. Possible photochemical and thermochemical reactions and ionization induced by the absorbing nanoparticles may also enhance drug delivery in solid tumors.

Low absorption of optical radiation by tissues and strong absorption by particles enhances drug delivery in tumors without damage to normal tissues. Laser ablation of the irradiated tissue surface is not induced, because the incident fluence of about 1 $J/cm^2$ is substantially lower than the tissue ablation threshold of 40–45 $J/cm^2$ at this wavelength. The particles should have high absorption coefficient ($10^4$–$10^6$ $cm^{-1}$), low emissivity, short lifetime of excited states, capability to bind to antibodies, low acute and chronic toxicity. Potential candidates are carbon, graphite, or metal (gold, silver, platinum) particles. Solid particles injected intravenously have low acute and chronic toxicity. Ideally, particles used for the drug delivery enhancement should be biodegradable. Insoluble liquid (for instance, liposomes) or biodegradable polymer particles can be stained with a strongly absorbing dye and used for the drug delivery enhancement instead of carbon or metal particles.

The ultrasonic "cold" cavitation enhances drug delivery from blood into cancer cells as in the case of laser-induced "hot" cavitation. The cavitation is induced by tensile (negative) pressure of the ultrasonic wave. The ultrasonic wave propagates through the skin and normal tissues with insignificant attenuation and induces cavitation upon interaction with the particles. It is known that cavitation threshold is substantially lowered by cavitation nuclei. The particles selectively delivered in tumor blood vessels and the interstitium are used as the nuclei decreasing cavitation threshold. Porous particles (such as activated carbon particles) with gas-filled pores can substantially lower cavitation threshold because they already have initial ("seed") bubbles.

Combination of laser-induced "seed" cavitation and the following bubble growth and collapse caused by ultrasonic waves can be applied for more efficient drug delivery in solid tumors. In this case, laser radiation initiates bubble formation producing cavitation nuclei while ultrasonic radiation increases dimensions of the bubbles, induces their oscillations and collapse resulting in microconvection.

Ultrasonic waves with moderate amplitude induce acoustic streaming (microconvection) near particles without cavitation, if their acoustic impedance is different from that of surrounding medium. The acoustic streaming may also enhance delivery of therapeutic agents from blood into tumor cells.

Pulsed microwave and radio-frequency radiation can induce local heating of absorbing particles (e.g., metal), because of its deep penetration into tissues and strong absorption in metals. However, the difference in absorption between metals and tissues is substantially less than in the case of visible or near infra-red radiation. In addition, generation and delivery of powerful short microwave or radio-frequency pulses to tumors are more complicated than the generation and delivery of short optical pulses.

Thermal and mechanical damage to endothelial cells of tumor vasculature induced by laser and ultrasonic radiation can be used for cancer treatment without drugs. Such damage results in the lack of blood supply to the tumor with the following avalanche death of cancer cells. Particle migration in the interstitium caused by interaction with laser or ultrasonic radiation induces thermal and mechanical damage to cancer cells that may result in death of cancer cells. Such an approach eliminates side effects of chemotherapy.

The following publications were referred to herein.

| U.S. Pat. No. 5,474,765 | Thorpe |
| U.S. Pat. No. 5,487,390 | Cohen et. al. |
| U.S. Pat. No. 5,543,158 | Gref et. al. |
| U.S. Pat. No. 5,651,986 | Brem et. al. |
| U.S. Pat. No. 5,565,215 | Gref et. al. |
| U.S. Pat. No. 5,578,325 | Domb et. al. |
| U.S. Pat. No. 5,614,502 | Flotte et. al. |
| U.S. Pat. No. 5,658,892 | Flotte et. al. |
| U.S. Pat. No. 5,660,827 | Thorpe et. al. |
| U.S. Pat. No. 5,718,921 | Mathiowitz et. al. |
| U.S. Pat. No. 5,713,845 | Tankovich |
| U.S. Pat. No. 5,762,918 | Thorpe |
| U.S. Pat. No. 4,971,991 | Imemura et. al. |
| U.S. Pat. No. 5,403,590 | Forse |
| U.S. Pat. No. 5,380,411 | Schlief |

Jain R. K. Science v. 271, pp. 1079–1080, 1996.
Curti B. D. Cancer Chemotherapy and Biotherapy. 1996, pp. 709–719.
Jain R. K. Sci. Am. v. 271, pp. 58–65, 1994.
Hopper R. W., et al., J. Appl. Phys. v. 41 (10), pp. 4023–4037, 1970.
Oku N., et al., Biol. Pharm. Bull. 20 (6), pp. 670–673, 1997.
Gref R., et al., Science v. 263, pp. 1600–1603, 1994.
Dvorak H. F., et al., Cancer Cells v. 3 (3), pp. 77–85, 1991.
Thorpe, et al., Breast Canc. Res. and Treatm. 36 (2), 237–251, 1995.
R. Pasqualini, et al., Nature v. 380, pp. 364–366, 1996.
W. Arap, et al., Science v. 279, pp. 377–380, 1998.
Takahashi T., Crit. Rev. Ther. Drug Carr. Syst. 2(3), pp. 245–274, 1986.
Mitragotri S., et al., Science, v. 269, pp. 850–853, 1995.
Johnson M. E., et al., J. Pharm. Sci. v. 85 (7), pp. 670–679, 1996.
Folkman J., Sci. Am. v. 275, pp. 150–154, 1996.
Esenaliev R. O.; et al., Appl. Phys. B v. 59, pp. 73–81, 1994.
Esenaliev R. O.; et al., Lasers Surg. Med. v. 13, pp. 470–484, 1993.
Esenaliev, et al., Lasers in the Life Science, 1994, 6(3), pp.153–161.
Esenaliev, et al., IEEE Trans. Biomed. Eng., 1989, 36, No12,1188–1194.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of enhancing anti-cancer drug delivery in a solid tumor, comprising the steps of:

administering at least one anti-cancer drug to said tumor;

injecting nanoparticles or microparticles to said tumor intravenously; and irradiating said tumor with radiation.

2. The method of claim 1, wherein said anti-cancer drug is selected from the group consisting of a monoclonal antibody, a cytokine, an antisense oligonucleotide, and a gene-targeting vector.

3. The method of claim 1, wherein said tumor is in an organ selected from the group consisting of breast, lung, brain, liver, skin, kidney, GI organ, prostate, bladder and gynecological organ.

4. The method of claim 1, wherein said nanoparticles or microparticles are long-circulating particles with or without antibody coating.

5. The method of claim 4, wherein said antibody is directed against tumor vasculature.

6. The method of claim 1, wherein said nanoparticle has a diameter from about 0.1 nm to about 7000 nm.

7. The method of claim 1, wherein said nanoparticle or microparticle is selected from the group consisting of a metal particle, a carbon particle, a graphite particle, a polymer particle, a liquid particle and a porous particle.

8. The method of claim 1, wherein said radiation is optical pulsed radiation generated from a laser or non-laser source.

9. The method of claim 8, wherein said optical radiation is delivered through skin surface or via optical fibers or endoscopes to said tumor.

10. The method of claim 8, wherein said optical radiation is in the spectral range from 0.2 $\mu$m to 2 $\mu$m.

11. The method of claim 1, wherein said radiation is utrasonic radiation generated from an ultrasonic transducer.

12. The method of claim 11, wherein said ultrasonic radiation is in the frequency range from 20 to 500 kHz.

13. The method of claim 11, wherein said ultrasonic radiation is delivered through skin surface to said tumor.

14. An anti-cancer drug delivery system, comprising:

a source of radiation;

an electronic system for monitoring of said radiation;

a means for delivery of said radiation to said tumor;

nanoparticles or microparticles absorbing said radiation;

an injection means for administration of said anti-cancer drug and said nanoparticles or microparticles in blood.

15. A method of treating a solid tumor, comprising the steps of:

injecting nano- or microparticles to said tumor intravenously; and irradiating said tumor with radiation.

* * * * *